(12) United States Patent
Piraino

(10) Patent No.: US 8,540,715 B2
(45) Date of Patent: Sep. 24, 2013

(54) LOCKING ROD FUSION DEVICE

(75) Inventor: Jason A. Piraino, Philadelphia, PA (US)

(73) Assignee: Temple University—Of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 13/128,445

(22) PCT Filed: Nov. 10, 2009

(86) PCT No.: PCT/US2009/063842
§ 371 (c)(1),
(2), (4) Date: Jun. 27, 2011

(87) PCT Pub. No.: WO2010/054363
PCT Pub. Date: May 14, 2010

(65) Prior Publication Data
US 2011/0251614 A1    Oct. 13, 2011

Related U.S. Application Data

(60) Provisional application No. 61/113,026, filed on Nov. 10, 2008.

(51) Int. Cl.
*A61B 17/72* (2006.01)
(52) U.S. Cl.
USPC ............................................. 606/62; 606/64
(58) Field of Classification Search
USPC ............... 606/59, 62–68, 87, 96, 97, 98, 104
See application file for complete search history.

(56) References Cited

U.S. PATENT DOCUMENTS

| 2,393,831 | A | * | 1/1946 | Stader | 606/56 |
| 4,338,927 | A | * | 7/1982 | Volkov et al. | 606/56 |
| 4,733,654 | A | * | 3/1988 | Marino | 606/64 |
| 6,572,620 | B1 | * | 6/2003 | Schon et al. | 606/62 |
| 6,579,293 | B1 | * | 6/2003 | Chandran | 606/64 |
| 6,860,902 | B2 | | 3/2005 | Reiley | |
| 6,932,818 | B2 | * | 8/2005 | Behrens | 606/64 |
| 7,314,488 | B2 | | 1/2008 | Reiley | |
| 7,410,488 | B2 | * | 8/2008 | Janna et al. | 606/62 |
| 7,465,303 | B2 | * | 12/2008 | Riccione et al. | 606/54 |

(Continued)

FOREIGN PATENT DOCUMENTS

WO   WO 2006120355 A1 * 11/2006

OTHER PUBLICATIONS

Brodsky et al.; WO 2006120355 A1; Nov. 2006; World Intellect [English machine translation].*
International Search Report for PCT/US2009/063842.

*Primary Examiner* — Jerry Cumberledge
(74) *Attorney, Agent, or Firm* — Caesar, Rivise, Bernstein, Cohen & Polotilow, Ltd.

(57) ABSTRACT

A locking rod fusion device and method uses internal locking rods and screws that will lock together. In particular, the device allows the insertion of multiple locking rods in combination with a plate, which requires less dissection and disruption of soft tissues and vasculature. The device also provides a more stable internal construct for fusions that prevent non-unions, hardware failure and reoccurrence of deformities, such as Charcot foot. The device combines the strength of locking technology and the utility and ease of an internal rod system to provide a single stable construct in multiple planes as apposed to using multiple plates or screws separately.

19 Claims, 18 Drawing Sheets

(56) References Cited

U.S. PATENT DOCUMENTS

| | | |
|---|---|---|
| 2005/0288792 A1 | 12/2005 | Landes |
| 2008/0221577 A1* | 9/2008 | Elghazaly .................... 606/64 |
| 2009/0099571 A1* | 4/2009 | Cresina et al. ................. 606/96 |
| 2010/0057133 A1* | 3/2010 | Simon .......................... 606/280 |
| 2010/0217327 A1* | 8/2010 | Vancelette et al. ............ 606/281 |

* cited by examiner

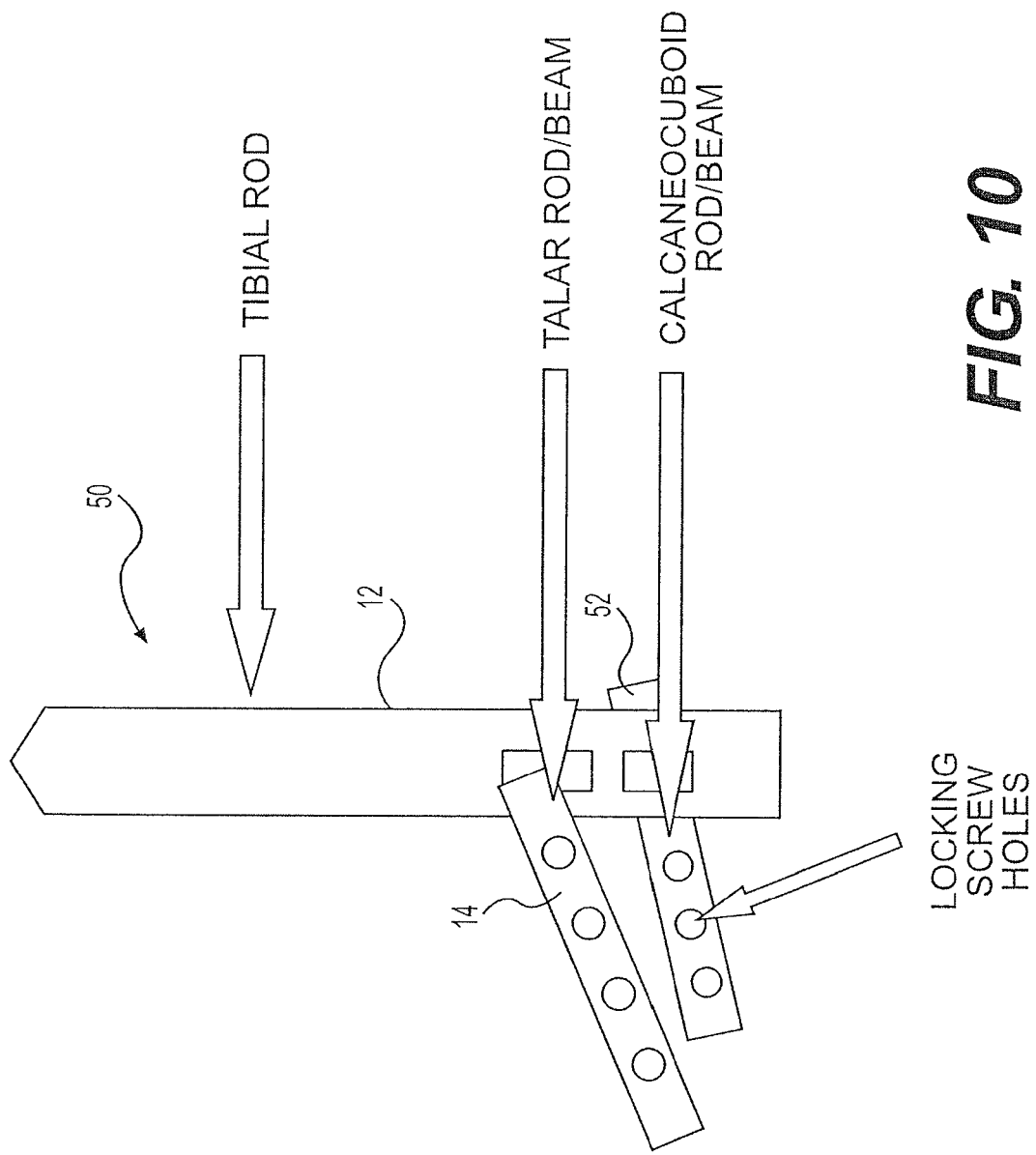

LOCKING ROD FUSION DEVICE

BACKGROUND OF THE INVENTION

1. Field of Invention

This invention relates to surgical devices, and more particularly, to surgically implantable bone support devices used to fuse bone structures.

2. Description of Related Art

Unfortunately, some patients suffer from various problems which require at least a portion of an ankle joint to be effectively immobilized. This is traditionally done by inserting one or more rigid rods or pins (typically made of stainless steel or titanium and having a diameter roughly the size of a patient's finger) into one or more bones in the ankle, and in the portion of the foot which includes the heel. This permanently affixes certain bones to other bones. The medical term for this type of permanent bone fixation is "arthrodesis".

While arthrodesis severely limits flexibility and mobility within the ankle joint, it sometimes becomes necessary as a treatment for conditions such as severe arthritis, infection and/or avascular necrosis of one or more bones in the region, congenital deformity of the tibio-talar or talocalcaneal joint, diabetic charcot foot or certain types of neuropathy. For these conditions, any motion of the bones relative to each other can cause severe pain in the foot or ankle, to a point where a patient becomes effectively unable to walk or put any pressure on that foot. Accordingly, immobilization of the ankle joint becomes an acceptable price to pay if the patient can begin to walk again without excruciating pain in the ankle and foot.

A bone plate is a plate that is traditionally fastenable to the surface of a fractured bone to support and/or stabilize the fracture as the bone heals. Bone plates may be attached to the bone with bone screws that extend from the plate into the bone. In some examples, the head of the bone screw is locked to the plate (e.g., by threaded engagement between the screw head and the bone plate) and in other plates the angle of the head of the screw is free to shift with respect to the plate, such that the screw may be placed in the bone at a surgeon-selected angle. In yet other examples, the screw head may cooperate with the bone plate to provide compression or distraction of the fracture Previously, problems of bone fixation have been addressed only in separate methods such as the use of internal rod or locking plate technology, which have been available for years in orthopedics. In other words, the current technology only contemplates either rods with locking screws, or plates with locking screws for fixation. These technologies are applied in one dimension, as no common approach has incorporated multiple techniques in three dimensions, regardless of a long-term need to immobilize the ankle joint.

The inventor has discovered that these existing approaches for bone fixation may still provide insufficient support for bone fusions, reconstructions and fracture management in the lower extremity (e.g., foot and ankle region). According the inventor has created an optimal single stable construct for ambulation by providing rods that lock together and use locking screws for internal fixation.

BRIEF SUMMARY OF THE INVENTION

The preferred embodiments include a locking rod fusion device including a vertical rod, an oblique rod, a locking plate and connecting rods. The oblique rod has a posterior end and an anterior tip, with the posterior end attached to the vertical rod. The oblique rod slants downward slightly from the posterior end to the anterior tip to establish a slightly obtuse angle between the vertical rod and the oblique rod such that when the vertical rod is inserted through a plantar foot, the oblique rod is aligned for insertion through the medial column. The locking plate is shaped to fit against an ankle bone, with the locking plate including a plurality of apertures aligned with the vertical rod, the oblique rod and bones in the foot when fit against the ankle bone. Of the connecting rods, a first connecting rod connects the locking plate to the vertical rod and a second connecting rod connects the locking plate to the oblique rod.

The preferred embodiments also include a locking rod fusion device including the vertical rod, the oblique rod, connecting rods and a calcaneocuboid rod. The oblique rod has a posterior end and an anterior tip, with the posterior end attached to the vertical rod. The oblique rod slants downward slightly from the posterior end to the anterior tip to establish a slightly obtuse angle between the vertical rod and the oblique rod such that when the vertical rod is inserted through a plantar foot, the oblique rod is aligned for insertion through the medial column. The calcaneocuboid rod has a posterior end and an anterior tip, with the posterior end attached to the vertical rod. The calcaneocuboid rod slants downward slightly from the posterior end to the anterior tip to establish a slightly obtuse angle between the vertical rod and the calcaneocuboid rod such that when the vertical rod is inserted through a plantar foot. The calcaneocuboid rod is aligned for insertion through the calcaneocuboid joint. Of the connecting rods, the first connecting rod connects the calcaneocuboid rod to the oblique rod and the second connecting rod locks the calcaneocuboid rod to an adjacent bone of the plantar foot.

As used herein, the terms "rod", "pin", and "nail" are used interchangeably. All three terms refer to a rigid elongated component that is inserted into one or more bones, rods or plates, for the purpose of anchoring, stabilizing, repairing, or supporting the bone(s), rod(s) or plate(s). The term "rod" usually implies a relatively large device, while the term "pin" implies a somewhat smaller device; however, there is no clear boundary between these terms. In addition, the term "rod" is not limited to a cross-sectional shape, and may in fact be circular, oval, square, rectangular, polygonal or any combination thereof, while still falling within the term "rod" as used herein.

As used herein, the term "non-threaded" indicates that a rod or pin does not have screw-type threads on its external surface; however, a non-threaded rod or pin can have one or more threaded holes passing through it, for fixation screws, so long as the threads are not exposed on the external surface. A rod externally threaded along at least a part thereof is generally referred to as a screw. The screws maybe threaded at one or both ends of the screws based on the preferred use of the screw. However, it should be noted that in some cases non-threaded rods or pins can be used and would still fall within the term "screw" as used herein, especially where the non-threaded screw is attached to another element (e.g., bone, plate, rod, pin) sufficiently to hold the rod to the element.

It should also be noted that, while the terms "rod", "pin", or "nail" normally tend to imply that an implant does not have an externally threaded surface, some people and some documents do not adhere to that convention, and some implanted rods, pins, or nails have external threads (including, in some cases, threads that are shallow and are not used to generate thrust or compression as the device is rotated). Accordingly, even though the vertical rods that have been used to date as disclosed herein have not had external threads, such rods can be provided with one or more externally threaded regions if desired, and would still fall within the term "rod" as used herein. All references cited herein are incorporated herein by reference in their entireties.

BRIEF DESCRIPTION OF SEVERAL VIEWS OF THE DRAWINGS

The invention will be described in conjunction with the following drawings in which like reference numerals designate like elements, and wherein:

FIG. 10 is a side view of another exemplary locking rod fusion device in accordance with the preferred embodiments;

DESCRIPTION OF PREFERRED EMBODIMENTS OF THE INVENTION

The preferred locking rod fusion system uses internal locking rods and screws that will lock together. In particular, the system allows the insertion of multiple locking rods in combination, which requires less dissection and disruption of soft tissues and vasculature. The system also provides a more stable internal construct for fusions that prevent non-unions, hardware failure and reoccurrence of deformities, such as Charcot foot. The system combines the strength of locking technology and the utility and ease of an internal rod system to provide a stable, single construct in multiple planes as apposed to using multiple plates or screws separately.

Figure 9:
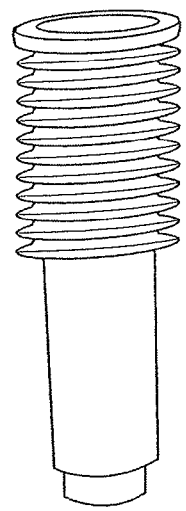
FIG. 9 is a view of an exemplary connecting rod.
Figure 8:
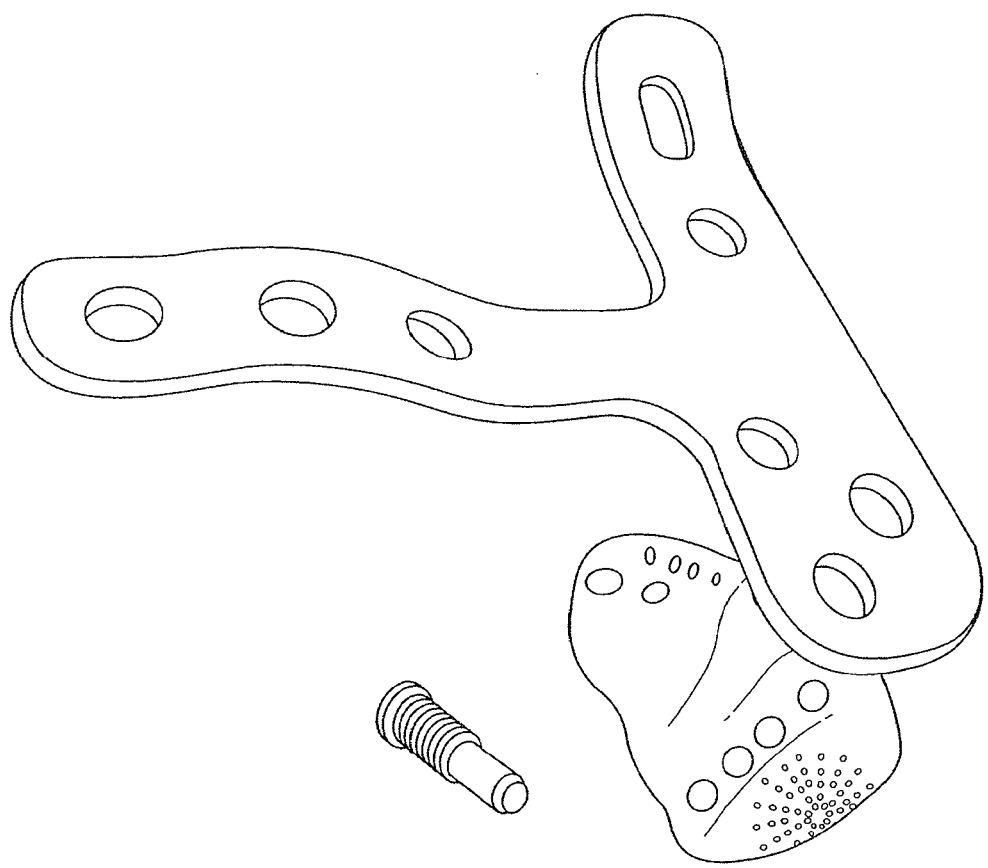
FIG. 8 is a view of the exemplary locking plate and foot alignment member.
Figure 12:
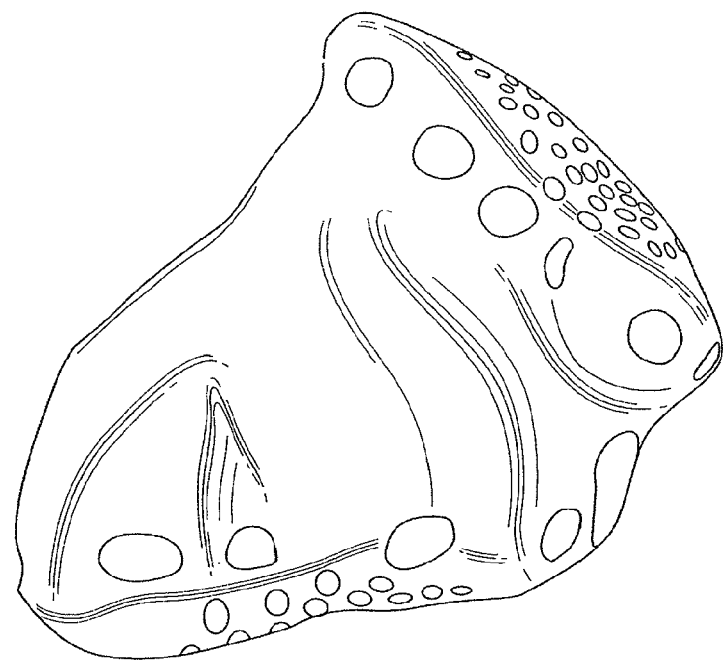
FIG. 12 is a second view of the foot alignment member of FIG. 6.
Figure 11:
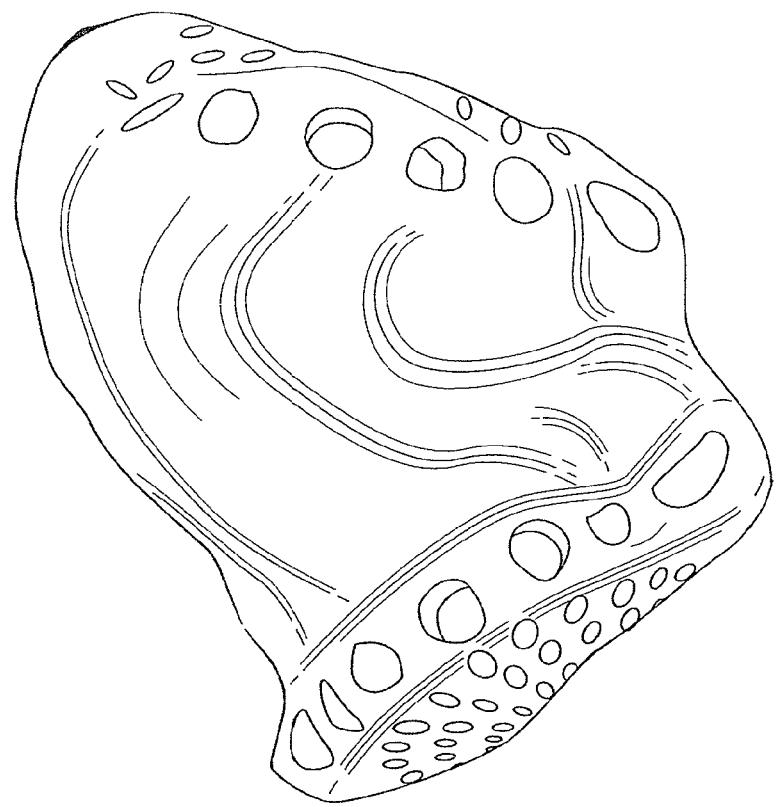
FIG. 11 is a first view of the foot alignment member of FIG. 6.
Figure 14:
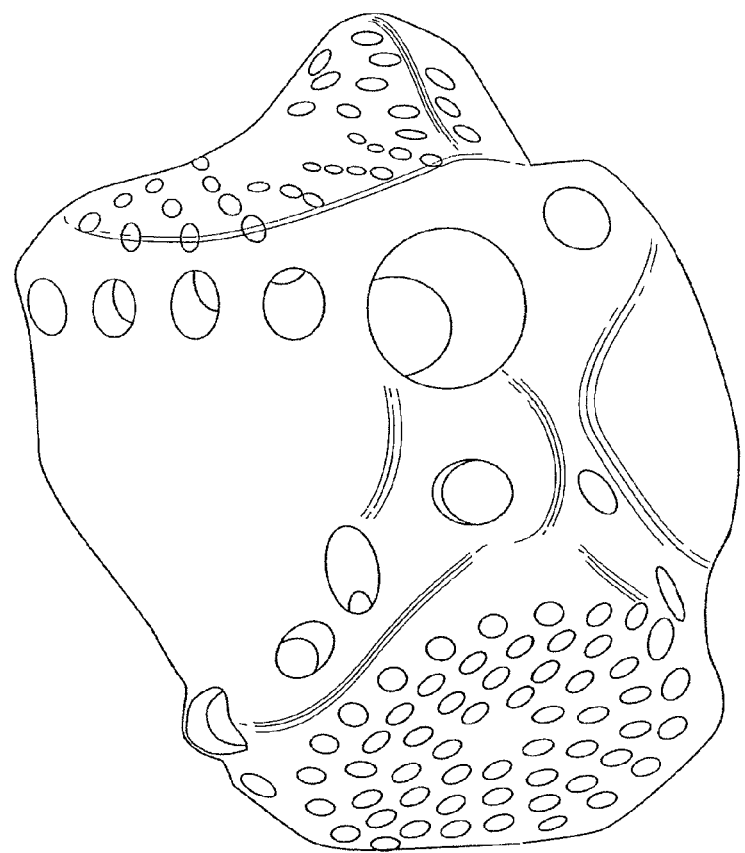
FIG. 14 is a fourth view of the foot alignment member of FIG. 6.
Figure 13:
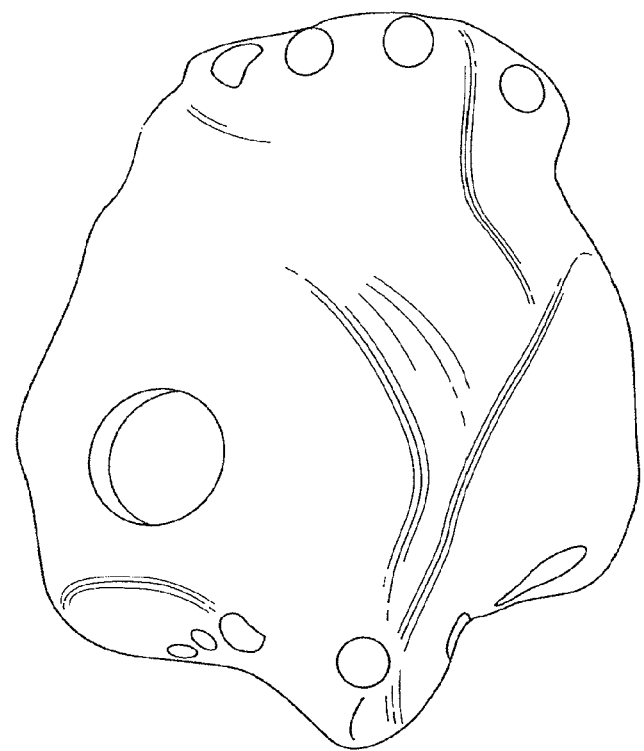
FIG. 13 is a third view of the foot alignment member of FIG. 6.
Figure 15:
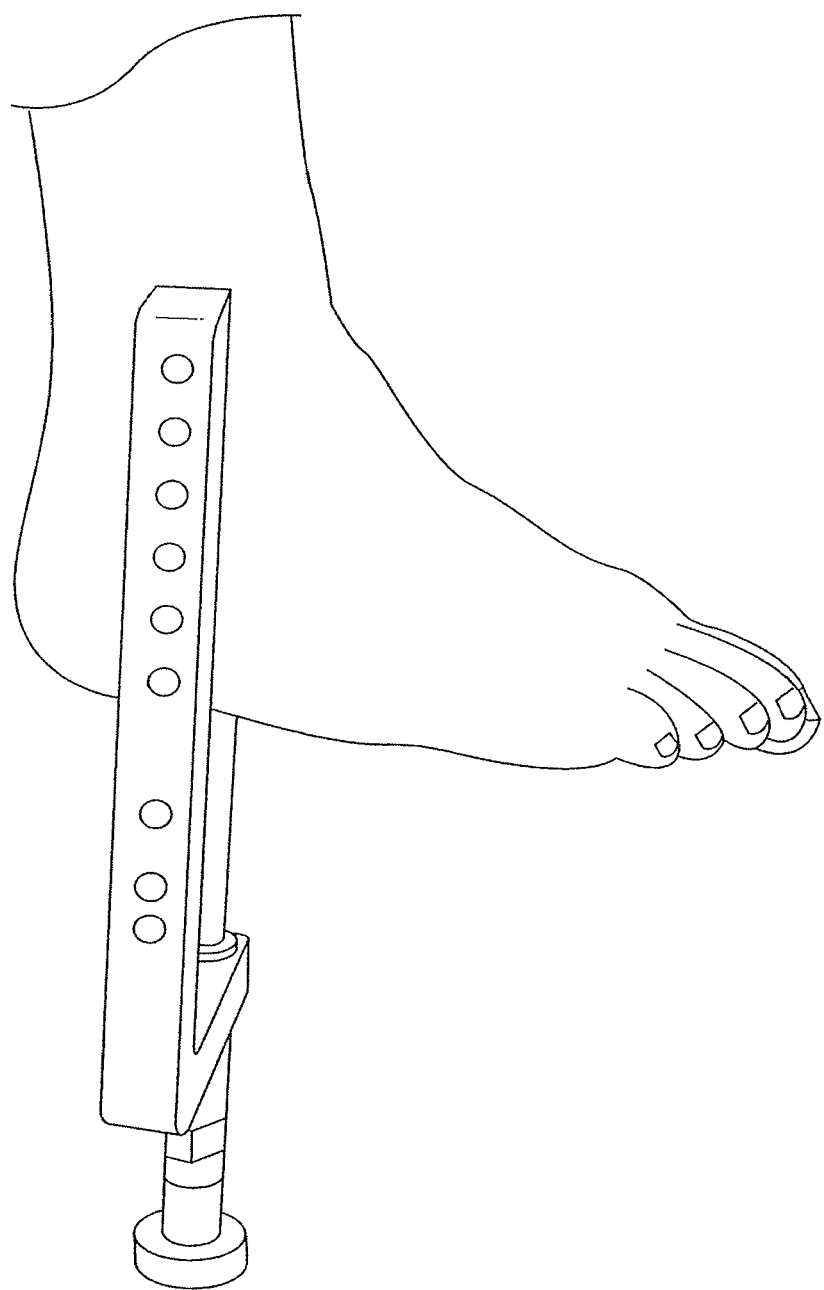
FIG. 15 is a first view showing an insertion of the vertical rod in a foot aided by an exemplary alignment jig.
Figure 16:
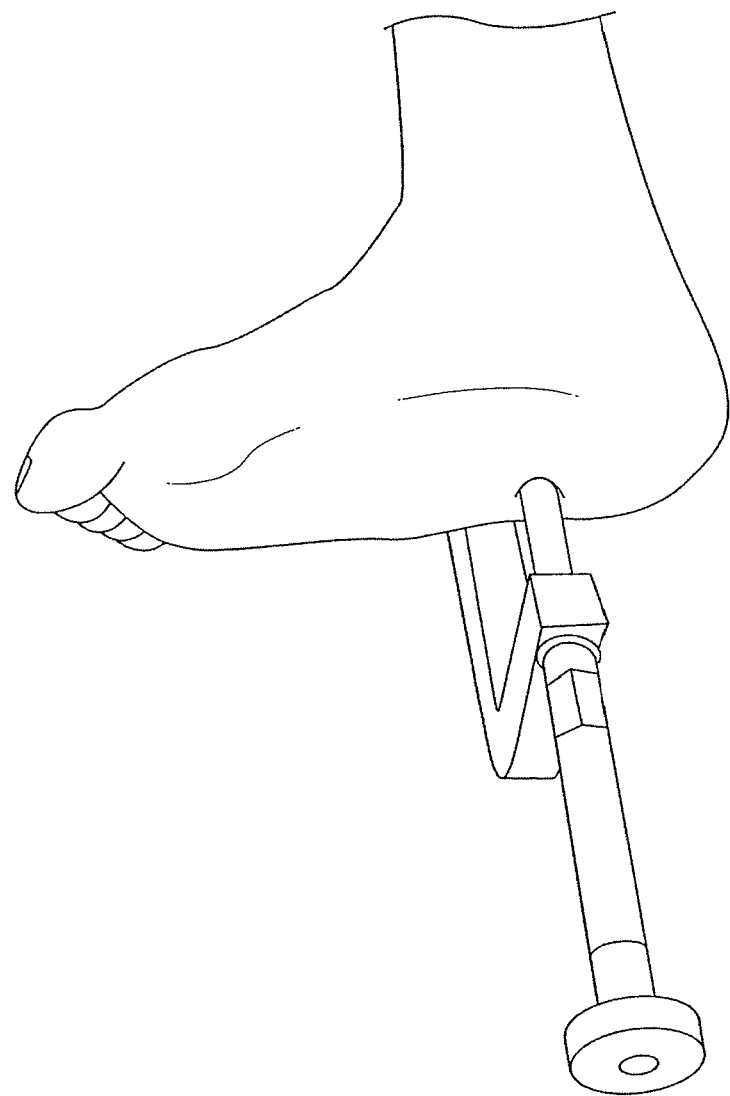
FIG. 16 is a second view showing an insertion of the vertical rod in a foot aided by the exemplary alignment jig.
Figure 17:
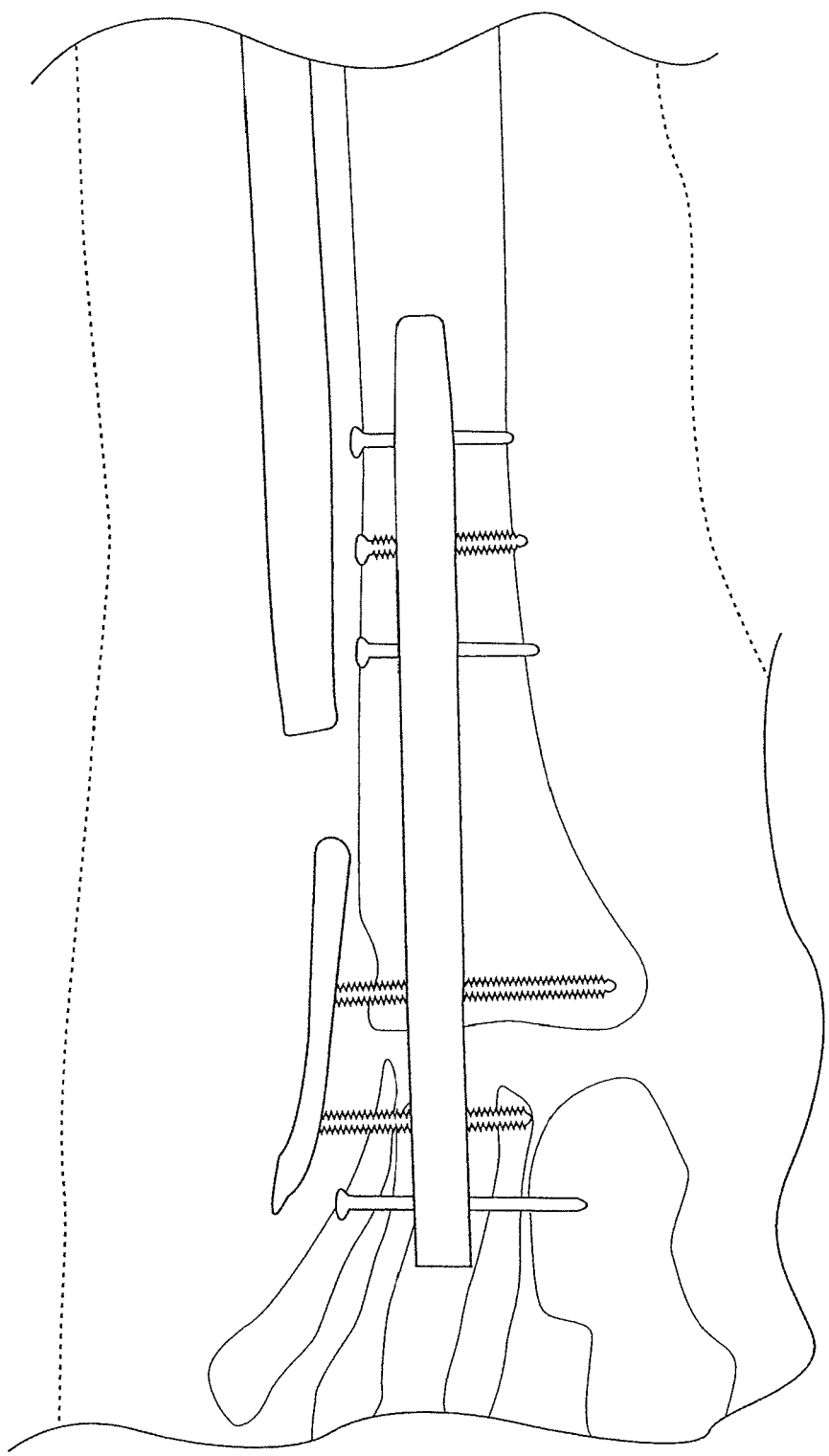
FIG. 17 is a first x-ray view showing an exemplary locking rod fusion device inserted into a foot.
Figure 18:
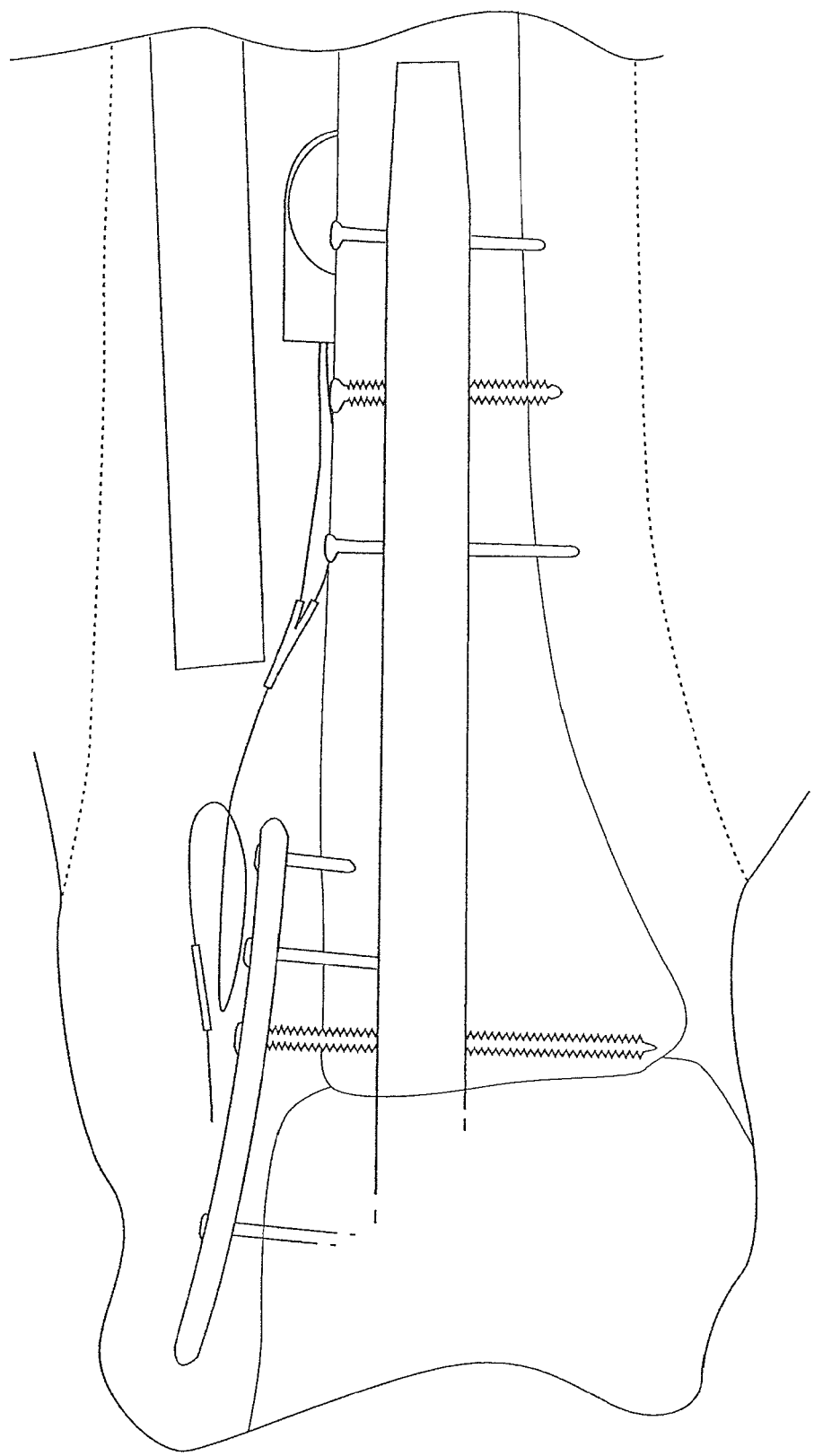
FIG. 18 is a second x-ray view showing an exemplary locking rod fusion device inserted into a foot.
Figure 19:
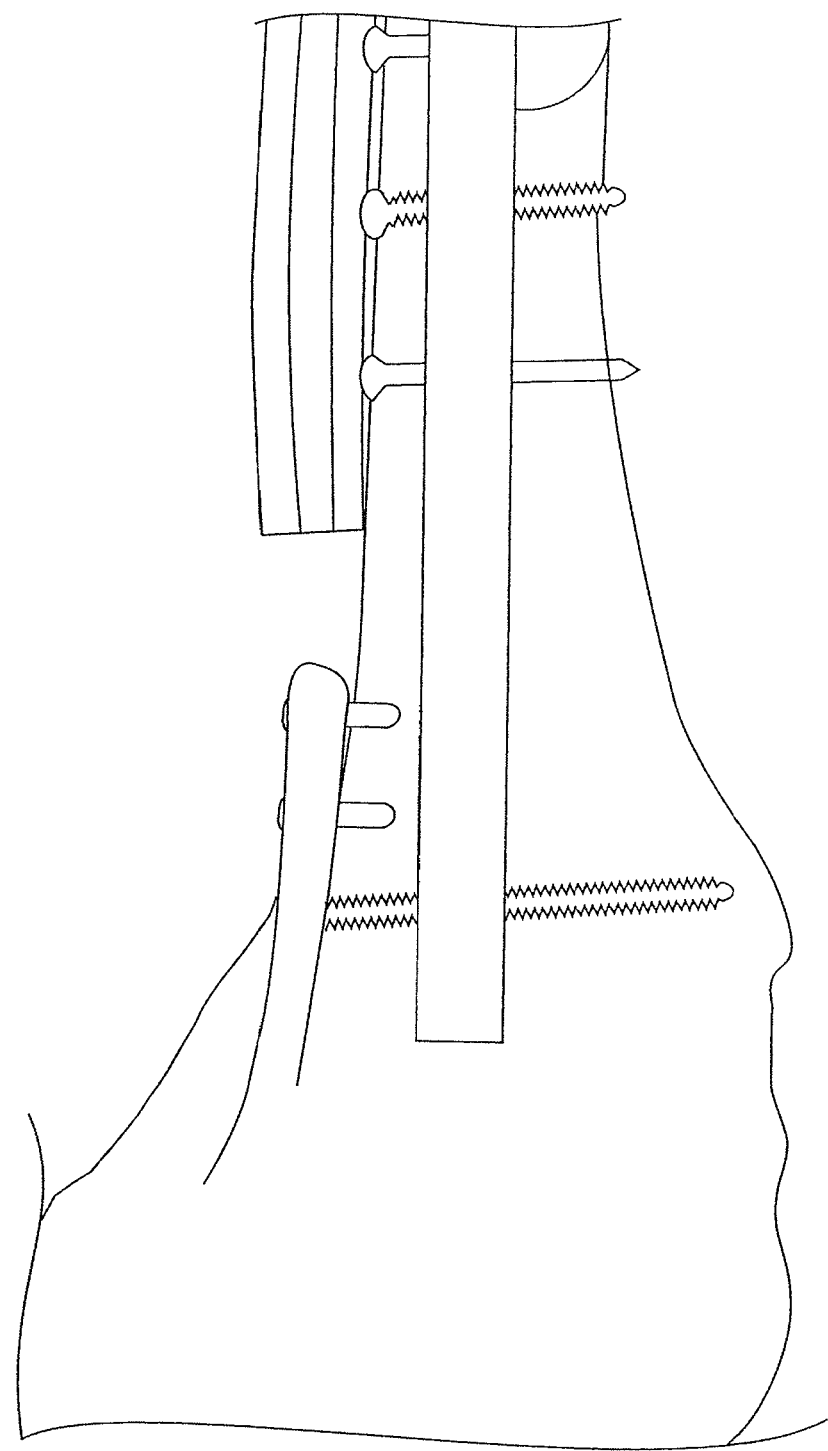
FIG. 19 is a third x-ray view showing an exemplary locking rod fusion device inserted into a foot.
Figure 20:
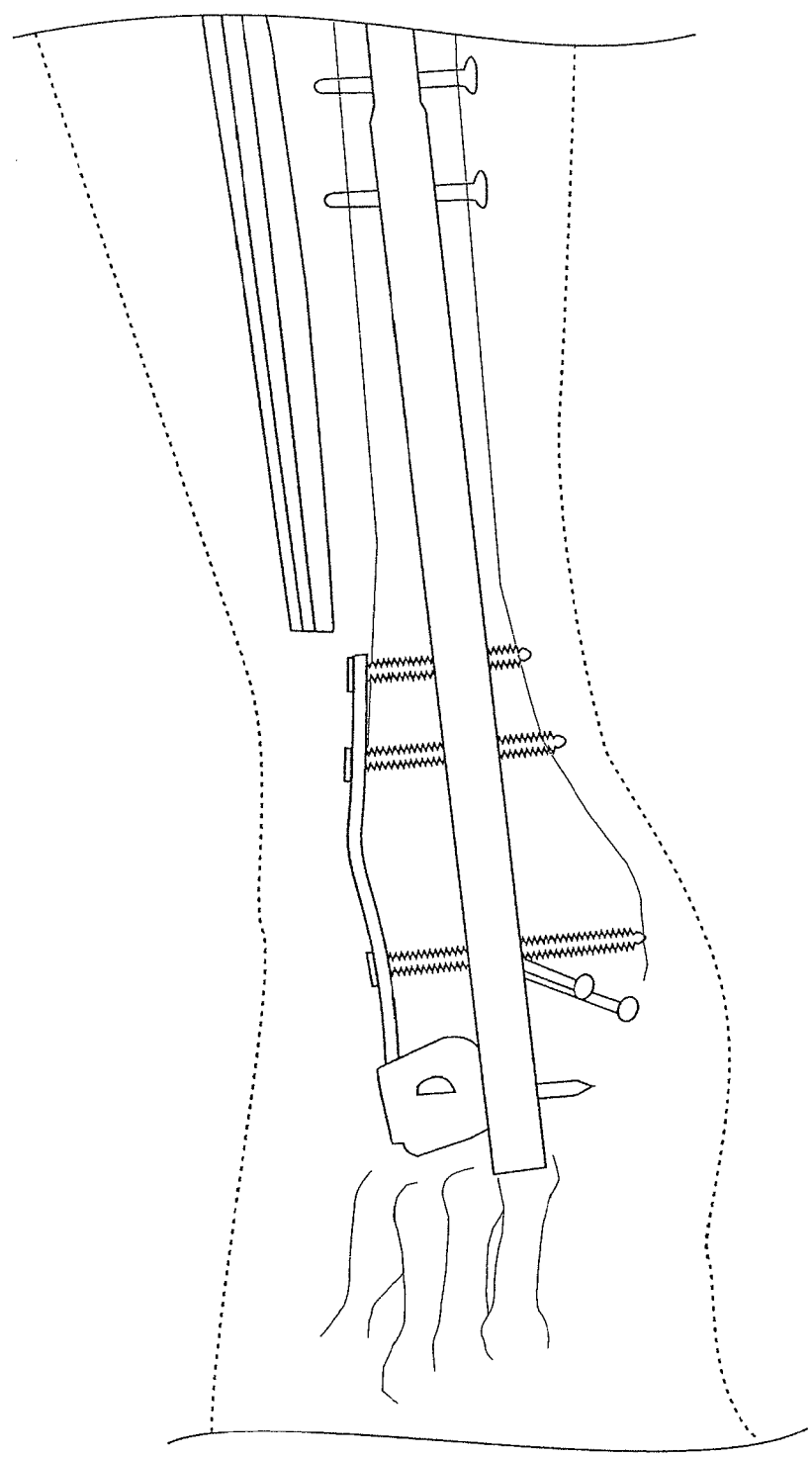
FIG. 20 is a fourth x-ray view showing an exemplary locking rod fusion device inserted into a foot.
Figure 21:
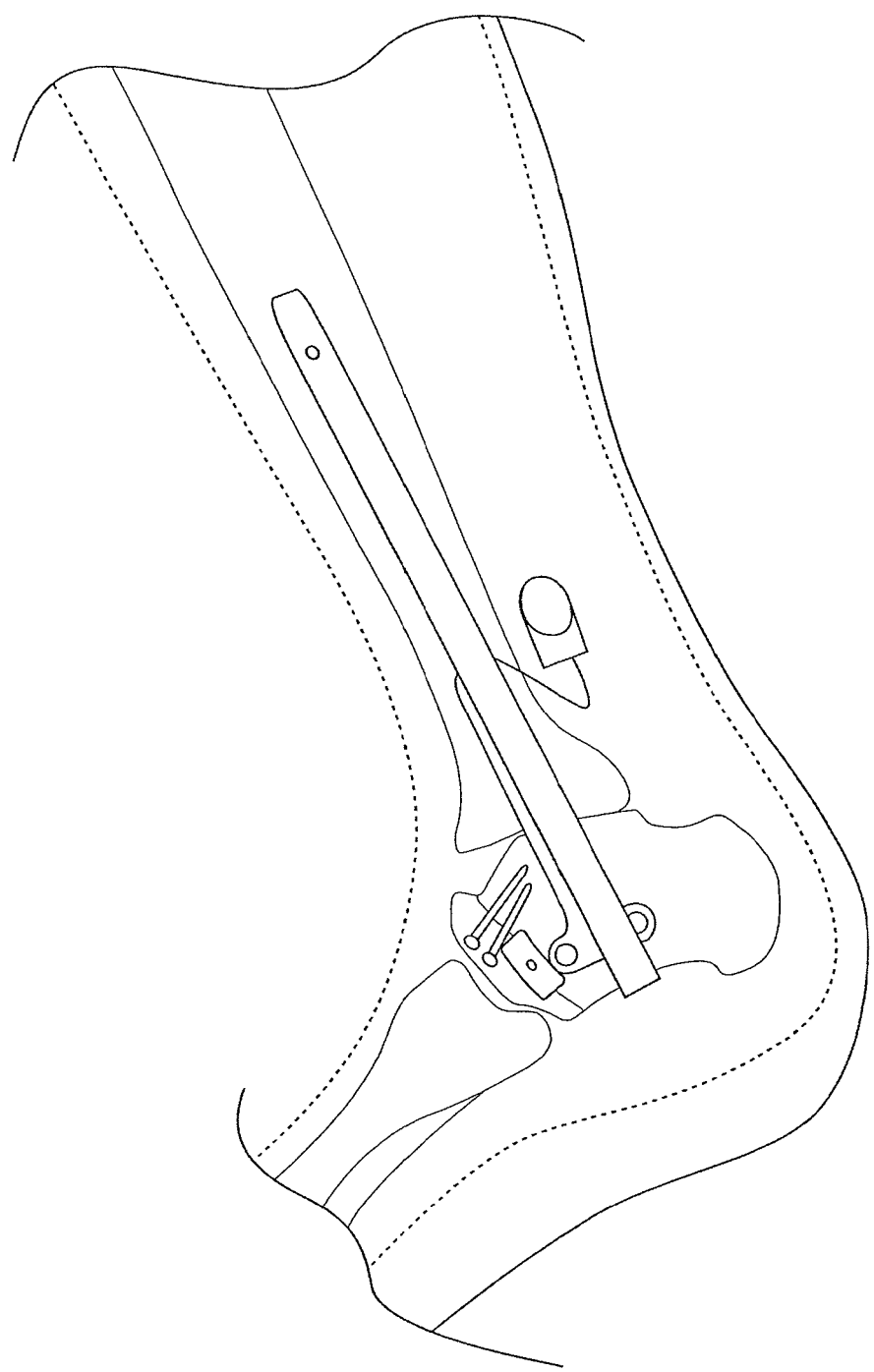
FIG. 21 is a fifth x-ray view showing an exemplary locking rod fusion device inserted into a foot.
Figure 22:
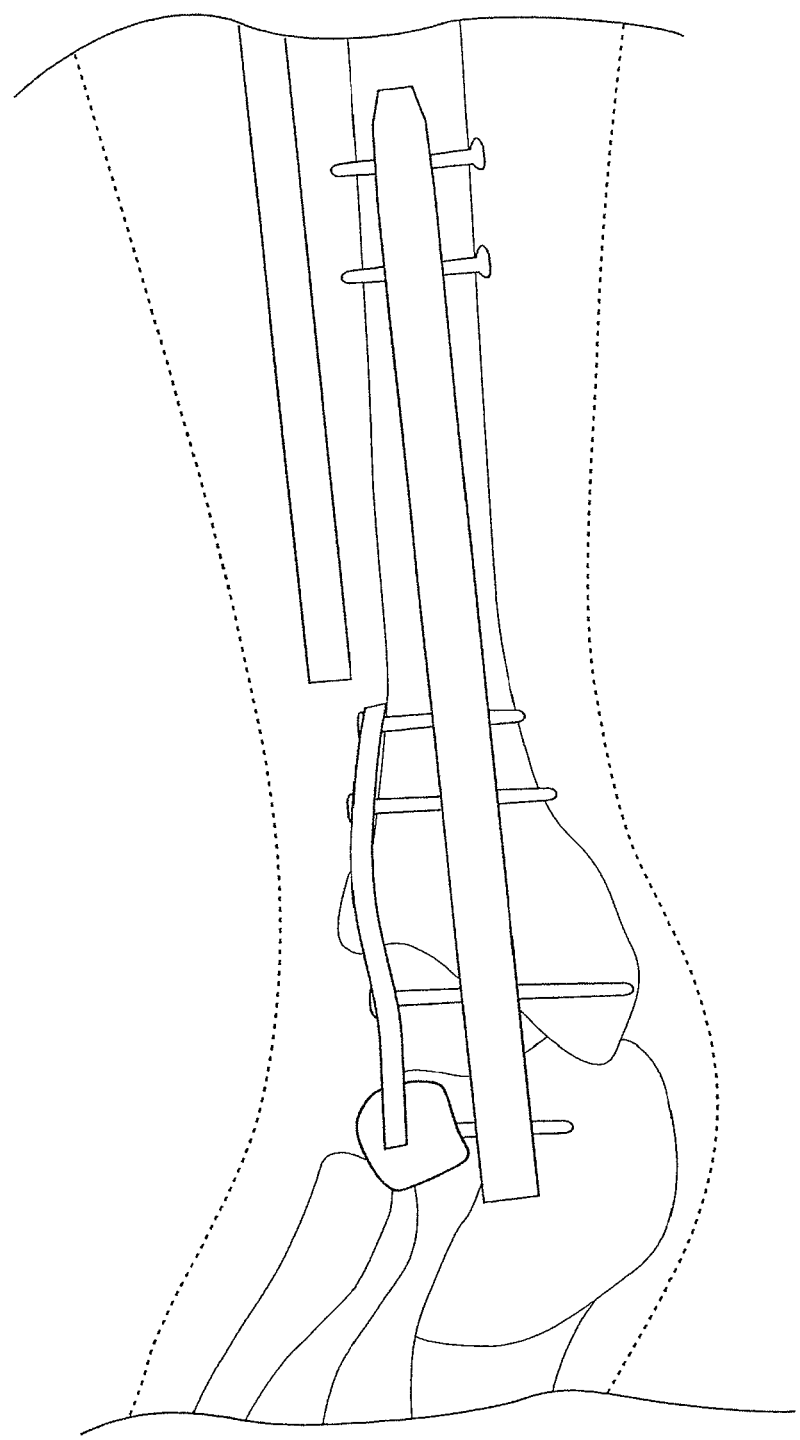
FIG. 22 is a sixth x-ray view showing an exemplary locking rod fusion device inserted into a foot.

In an exemplary embodiment, the locking rod fusion system 10 includes a vertical rod 12, an oblique rod 14, a locking plate 16 (FIG. 8), and a plurality of connecting screws or rods 18 (FIG. 9). When fully assembled, as shown, for example, in FIGS. 1-5, the oblique rod 14 slants downward slightly, from its posterior end 20, through the vertical rod 12 to its anterior tip 22. This establishes a slightly obtuse angle between the vertical rod 12 and the oblique rod 14, such that when the vertical rod is inserted through the plantar foot (e.g., the calcaneal, the talus and the tibia), the oblique rod is aligned for insertion through the medial column (e.g., the talus, navicualar, medial cuneiform, and/or first metatarsal).

Figure 1:
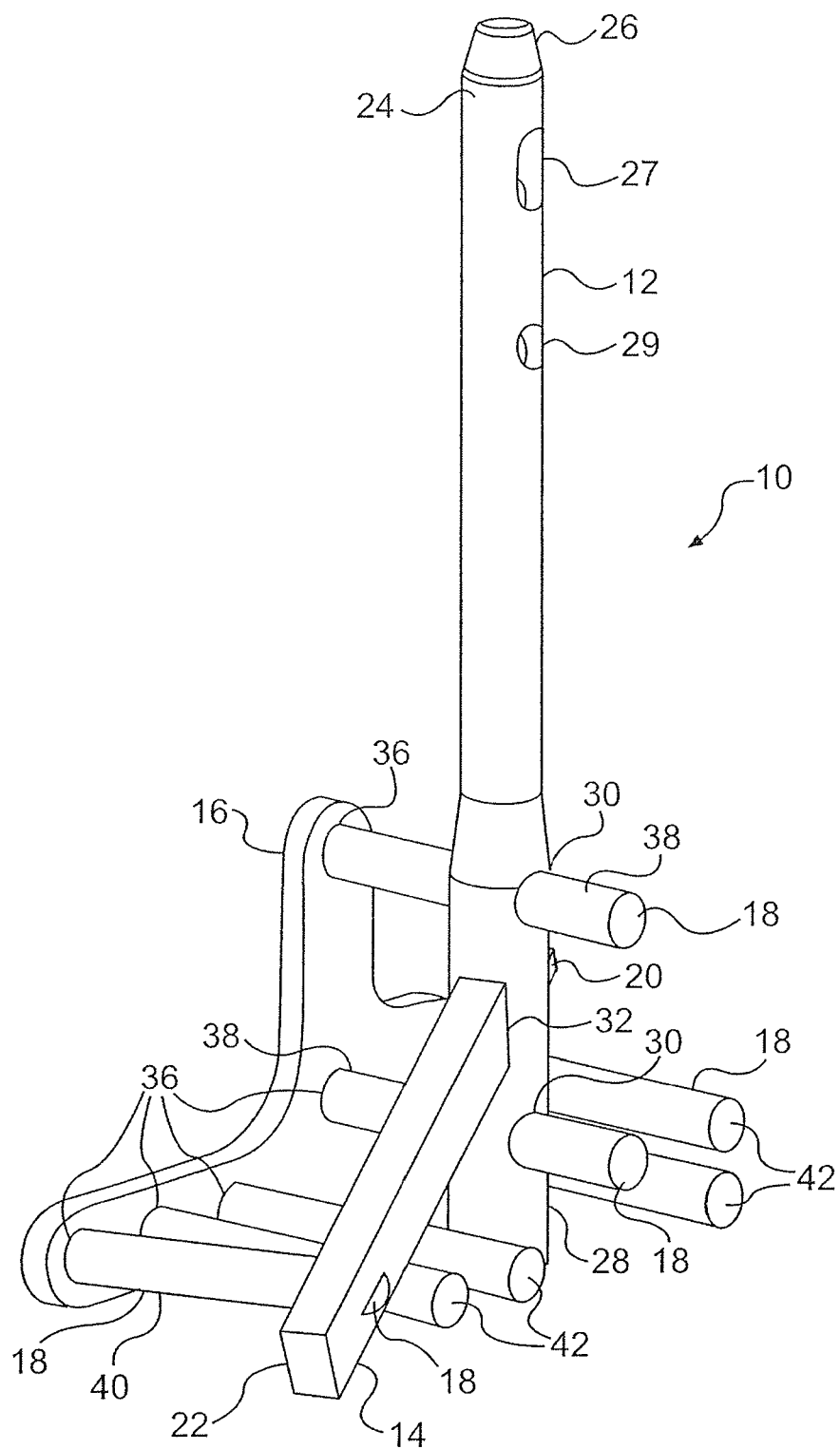
FIG. 1 is a first view of an exemplary locking rod fusion device in accordance with the preferred embodiments.
Figure 2:
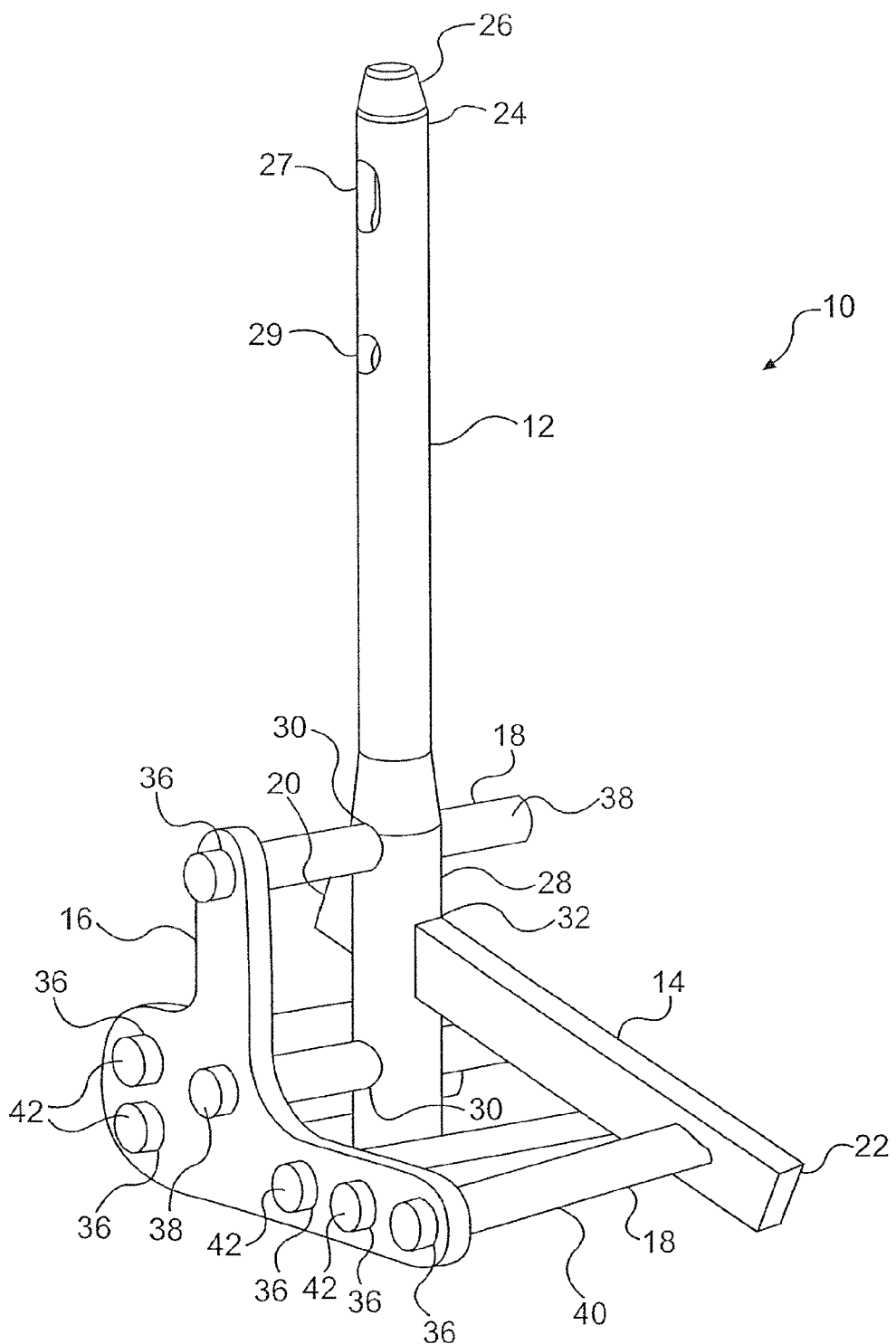
FIG. 2 is a second view of the exemplary locking rod fusion device in accordance with the preferred embodiments.
Figure 3:
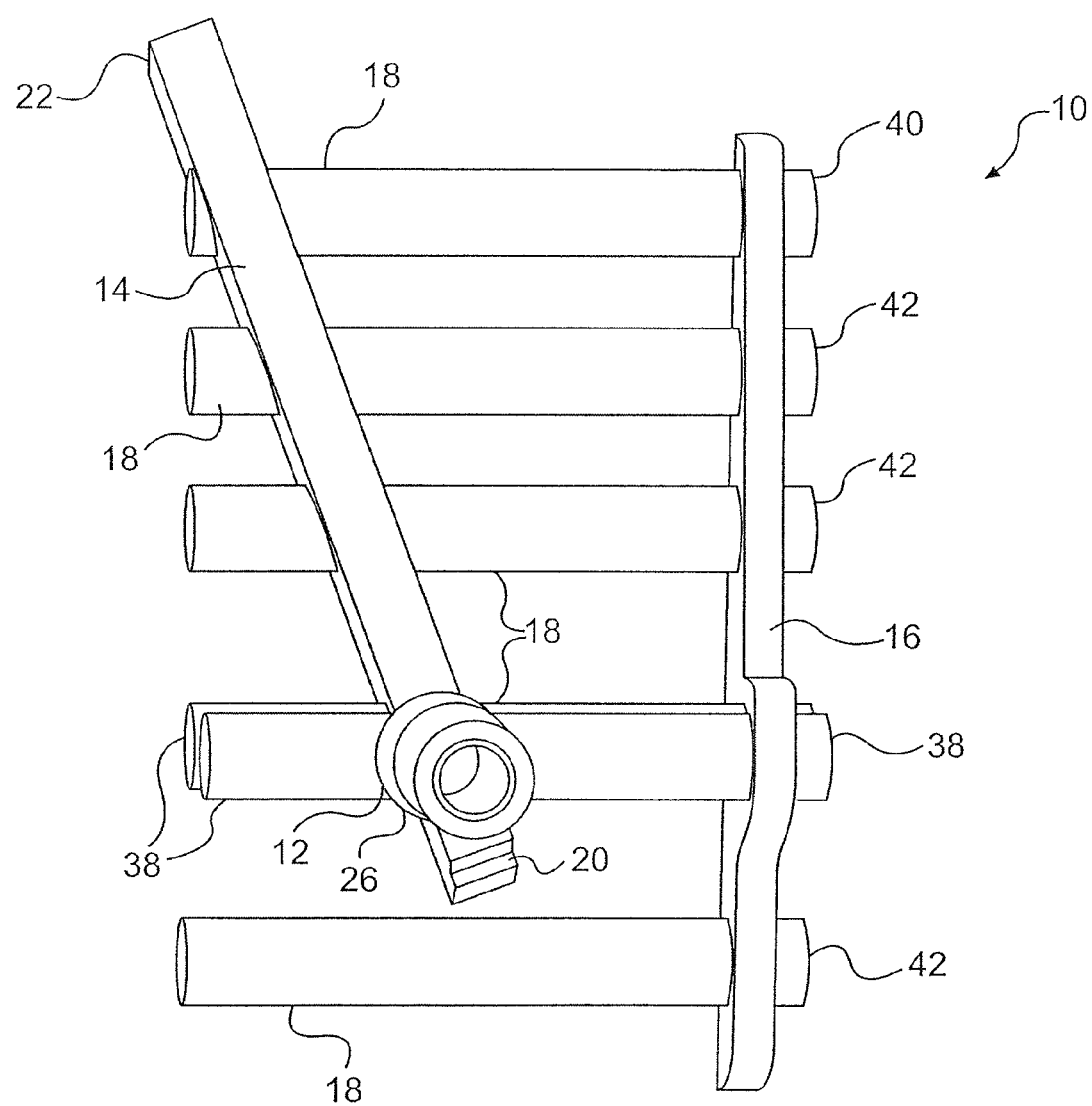
FIG. 3 is a top view of the exemplary locking rod fusion device in accordance with the preferred embodiments.

As can best be seen in FIGS. 1 and 2, the vertical rod 12 includes a distal region 24 with a tapered end 26 for more efficient insertion into the lower extremity of the patient, and a proximal region 28 preferably wider in diameter than the distal region for added strength and stability during use. The distal region 24 includes alignment apertures 27, 29 for alignment as needed. The proximal region 28 includes threaded apertures 30 for alignment, which are preferably internally threaded to receive screws that connect the vertical rod to the locking plate, as described for example in greater detail below. The proximal region 28 also includes an oblique rod aperture 32 sized and aligned to hold the oblique rod 14 at its obtuse angle aligned with the medial column.

In a preferred embodiment the oblique rod aperture 32 includes a cylindrically bored and internally threaded to receive and hold the oblique rod, which in the embodiment is cylindrical and externally threaded to couple to the oblique rod aperture. In the embodiment depicted in FIGS. 1-3, the oblique rod 14 and oblique rod aperture 32 are not threaded, but shaped for frictional engagement. In these alternative embodiments the oblique rod and matching aperture are shaped and sized for frictional engagement therebetween and their respective shapes are not otherwise limited. For example, the oblique rod 14 is generally shown having either a circular or rectangular cross section and is preferably tapered at its distal end for easier insertion within the medial column. However, as noted above, the shape of the rod is not so limited other than sized to fit in the medial column of the patient.

Preferably, and in particular when not threaded, the oblique rod 14 is locked to the vertical rod 12 within the oblique rod aperture with a screw 34. The screw 34 is inserted through an aperture of the vertical rod, such as at the base of the vertical rod, that is internally threaded to receive the screw 34, which abuts against the oblique rod 14 to lock the rod in place.

The locking plate 16 is shaped to fit against the tibia, talus, calcaneus and cuboid, preferably subcutaneously at the outer ankle and foot. The locking plate 16 includes a plurality of apertures 36 aligned with the vertical rod 12, the oblique rod 14 and different bones in the foot. The apertures 36 are preferably internally threaded to match externally threaded screws sized to connect the locking plate to the vertical rod 12, the oblique rod 14 and bones in the foot. If not internally threaded, the apertures 36 are sized to abut the head of rods preferably externally threaded at their distal end to attach to the rods 12, 14 and bones.

As can be seen in the drawings, first screws 38 attach and lock the locking plate 16 to the vertical rod 12, which includes internally threaded bores aligned with matching respective apertures 36 of the locking plate 16 to receive the first screws 38. A second screw 40 attaches and locks the locking plate 16 to the oblique rod 14, which has an internally threaded bore aligned with a respective aperture 36 to receive the second screw 40. Third screws 42 engage with respective apertures aligned with respective bones in the foot to attach the respective bones to the plate. It is understood that the screws may have different diameters at distal and proximal ends thereof to fit into respective bores or apertures of the locking structures. For example, the threaded bore of the oblique rod 14 may be smaller in diameter than the aperture 36 due to size limitations of the oblique bore within the medial column.

Figure 4:
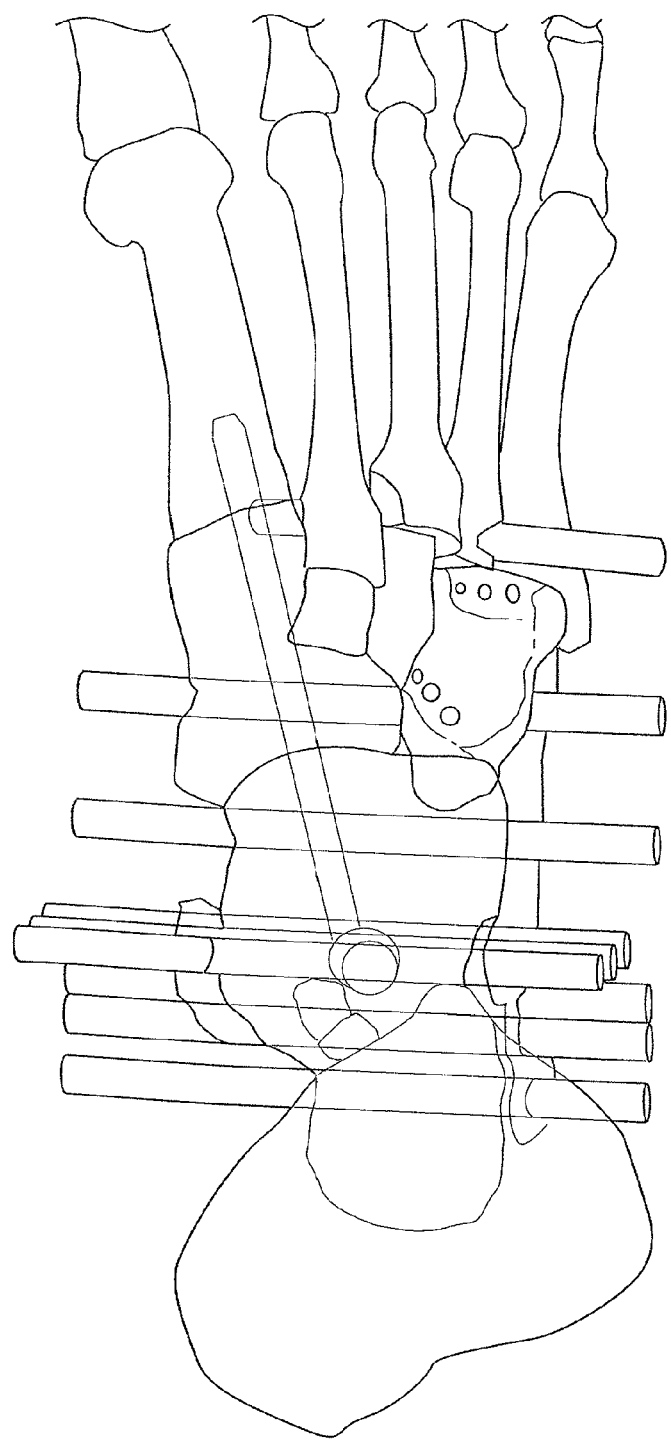
FIG. 4 is a top view of the exemplary locking rod fusion device inserted into an exemplary foot.
Figure 5:
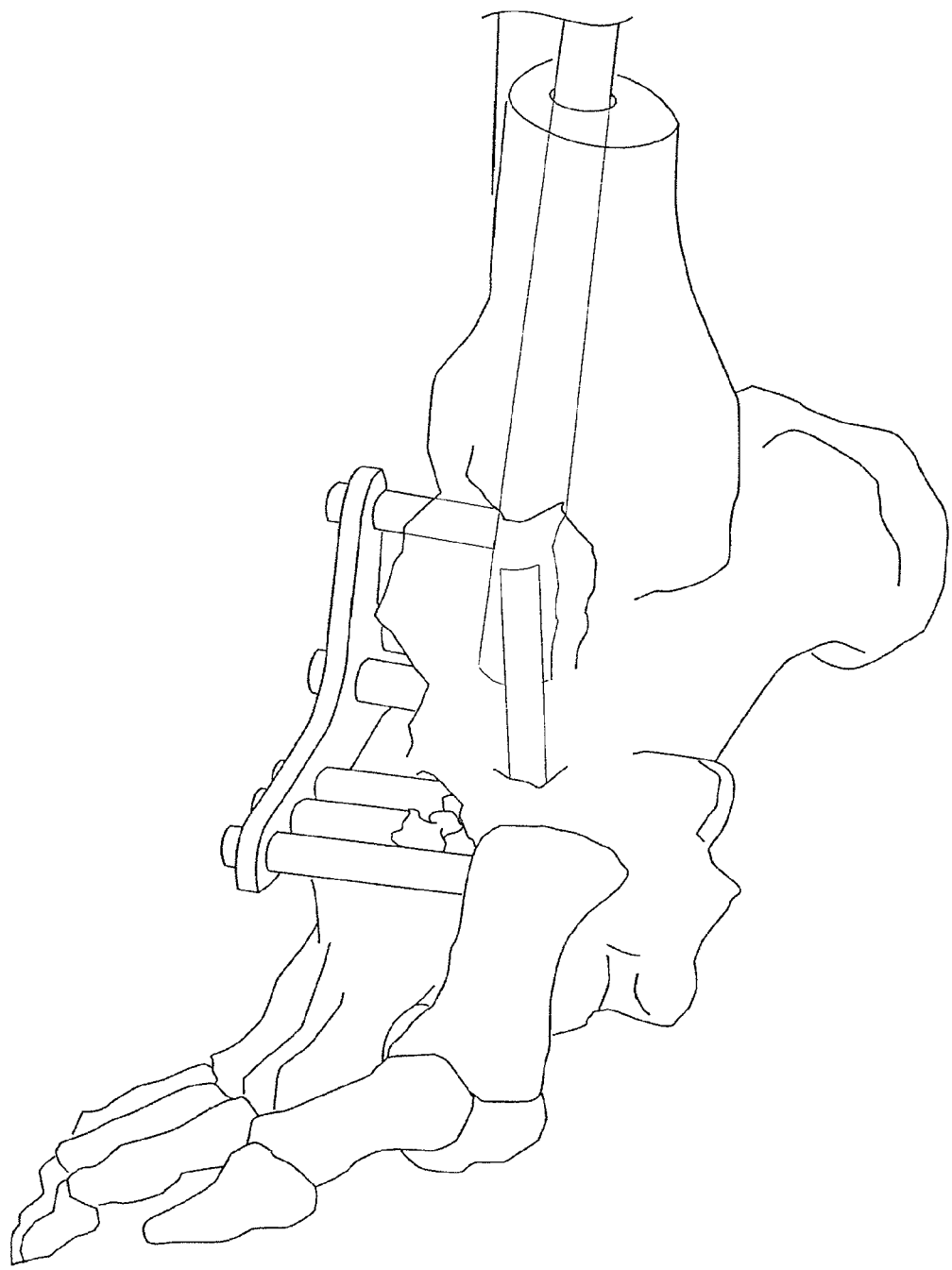
FIG. 5 is a plan view of the exemplary locking rod fusion device shown in FIG. 4.

As can be seen in FIGS. 4 and 5, when fully inserted and assembled in a lower extremity of a patient, the locking rod fusion system locks the bones in the region together and immobilizes the ankle joint so the patient can walk again without excruciating pain in the ankle and foot. While not being limited to a particular theory, the locking device is applied to the patient as set forth by example below.

Figure 7:
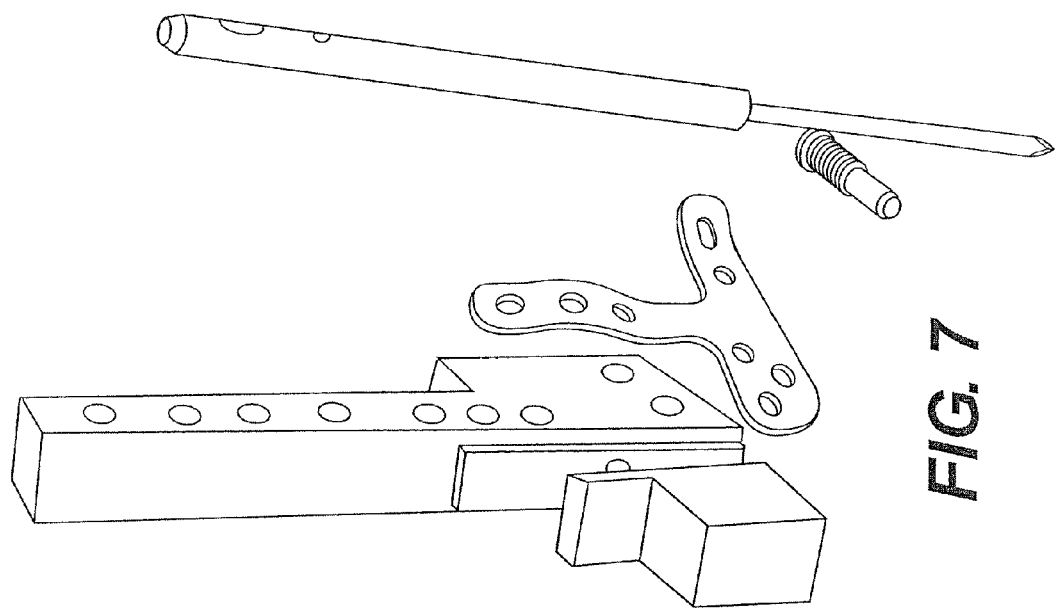
FIG. 7 is a view of an exemplary alignment jig, vertical rod and locking plate.
Figure 6:
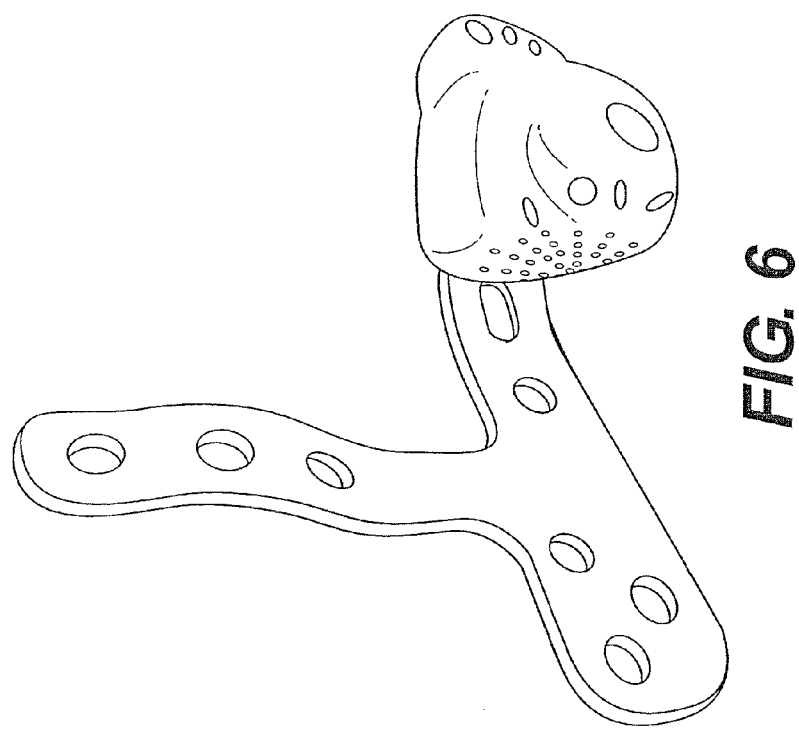
FIG. 6 is a view of an exemplary locking plate and foot alignment member.

1. Create lateral exposure to access the lateral structures, this includes releasing the Achilles tendon.
2. Prepare the ankle, subtalar, and calcaneocuboid joints for fusion.
3. Make a Plantar incision in the foot where the rod will be inserted.
4. Insert a guide wire through the plantar foot, for example through the calcaneus, talus and tibia, check its position under intra-operative fluoroscopy.
5. Insert a drill over the guide wire and drill the canal.
6. After drilling is complete, place flexible reamers through the canal and ream the site to 1 mm less than the diameter of the rod 12.
7. Insert the medial column drill guide into the canal so that the guide hole is centrally located in the talus using an alignment jig (FIG. 7) configured specifically for alignment of the rods, screws and plate of the locking system.
8. Confirm the position of the guide in the canal under intra-operative fluoroscopy.
9. Prepare and aligned the medial structures for fusion; insert the drill sleeve through the alignment jig and drive the guide pin through the drill guide and medial column so that the guide wire is driven centrally through the medial column (e.g., talus, navicualar, medial cuneiform, and/or first metatarsal).
10. Drill and ream the medial column to 0.5 mm less than the size of the oblique rod 14.
11. Remove the drill guide from the central canal.
12. Insert the vertical rod 12, otherwise described as the Tibial, Talar, Calcaneal (TTC) rod into the central canal.
13. Insert the oblique rod 14 through the vertical or TTC rod 12 and through the medial column. If threaded, tighten and lock the oblique rod to the vertical rod and proceed to step 15 if desired.
14. Target the proximal screws (Tibial) using the alignment jig.
15. Drill as needed and insert a proximal screw into the vertical rod and abut the oblique rod to lock the oblique rod against the vertical rod.
16. Align the lateral locking plate along the Tibia, Talus, calcaneus and cuboid.
17. Insert locking towers through the jig to target the distal bores of the vertical TTC rod
18. Engage the locking towers in the locking apertures of the plate so that the drill holes of the plate and vertical rod are identical.
19. Drill holes between respective matching apertures/bores of the locking plate 16 and vertical rod 12; insert the locking screws 38 through the locking plate towards the vertical rod so that the distal screw threads of the locking screws thread (lock) into the vertical rod and the threaded proximal locking head threads (locks) into the plate until all of the distal holes in the vertical rod are locked to the plate.
20. Drill a hole between a respective matching aperture/bore of the locking plate 16, bones of the medial column, and the oblique rod 14; insert a locking screw 40 through the locking plate towards the oblique rod so that the distal screw threads of the locking screws thread (lock) into the oblique rod and the threaded proximal locking head threads (locks) into the plate to lock the rod to the plate.
21. Drill holes from remaining apertures in the locking plate 16 into respective bones in the foot, and insert locking screws 42 through the holes to secure and lock the plate to the drilled bones. These last two steps are interchangeable.
22. Check the final alignment using fluoroscopy.

In another example of the preferred embodiments, a locking rod fusion system 50 includes a vertical (tibial) rod 12, an oblique (talar) rod 14, a calcaneocuboid rod 52, and a plurality of connecting screws or rods 18. As can best be seen in FIG. 10, the oblique (talar) rod 14 slants downward slightly through a first downward slanting opening of the vertical (tibial) rod, from the oblique rod's posterior end 20, through the vertical (tibial) rod 12 to its anterior tip 22. Likewise the calcaneocuboid rod 52 slants downward slightly, preferably even less slightly than the oblique rod, through a second downward slanting opening in the vertical (tibial) rod. The orientation of the calcaneocuboid rod 52 after insertion through the vertical rod 12 establishes a slightly obtuse angle between the vertical rod 12 and the calcaneocuboid rod 52, such that when the vertical rod is inserted through the plantar foot (e.g., the calcaneal, the talus and the tibia), the calcaneocuboid rod is aligned directed laterally for insertion into the calcaneocuboid joint to help fuse that joint.

This alternative exemplary system 50 gives the physician the option of using a locking plate with the Tibial rod, or a second "beam" inserted through the tibial rod crossing the calcaneocuboid joint. As noted above, this variation includes a second distal hole (i.e., the second downward slanting opening) in the vertical (tibial) rod 12 that allows insertion of the calcaneocuboid rod 52 for insertion through the posterior calcaneus, through the vertical tibial rod, through the calcaneocuboid joint and preferably ending in the cuboid. This calcaneocuboid rod 52 is inserted in the same fashion as the oblique (talar) rod 14 (i.e., by drilling and insertion of the beam which may or may not be locked into the vertical (tibial) rod 12). The calcaneocuboid rod 52 preferably can also accept locking screws from the lateral calcaneus and cuboid.

It should be noted that the vertical (tibial) rod 12 is shown in FIG. 10 longitudinally rotated 90 degrees from its preferred orientation to show the first and second slightly downward slanting openings that hold and align the oblique (talar) rod 14 and the calcaneocuboid rod 52 respectively during use. It should also be noted that the oblique (talar) rod 14 and the calcaneocuboid rod 52 are shown in FIG. 10 longitudinally rotated from their preferred orientation to show apertures in the rods for connecting the rods together with connecting screws or rods 18 as similarly described in the examples above. It should be understood that during use the apertures are aligned with the other rod or bones in the foot. While not being limited to a particular theory, the calcaneocuboid rod 52 is preferably used instead of the plate 16. However, it is understood that both the calcaneocuboid rod 52 and the plate 16 could be used together or alternatively within the scope of the preferred embodiments.

It is understood that the method and apparatus for making the locking rod fusion system described herein are exemplary indications of preferred embodiments of the invention, and are given by way of illustration only. In other words, the concept of the present invention may be readily applied to a variety of preferred embodiments, including those disclosed herein. While the invention has been described in detail and with reference to specific examples thereof, it will be apparent to one skilled in the art that various changes and modifications can be made therein without departing from the spirit and scope thereof Without further elaboration, the foregoing will so fully illustrate the invention that others may, by applying current or future knowledge; readily adapt the same for use under various conditions of service.

What is claimed is:

1. A locking rod fusion device, comprising:
   a vertical rod;
   an oblique rod having a posterior end and an anterior tip, the posterior end attached to the vertical rod, the oblique rod slanting downward slightly from the posterior end to the anterior tip to establish a slightly obtuse angle between the vertical rod and the oblique rod such that when the vertical rod is inserted through a plantar foot, the oblique rod is aligned for insertion through the medial column;
   a locking plate implant lockingly attached to the vertical rod and the oblique rod, the locking plate implant shaped to fit against an ankle bone, the locking plate implant including a plurality of apertures aligned with the vertical rod, the oblique rod and bones in the foot when fit against the ankle bone;
   a first connecting rod directly attached to the locking plate implant and the vertical rod, the locking plate implant and the vertical rod having a locked engagement therebetween from the direct attachment of said first connecting rod to the locking plate implant and the vertical rod; and
   a second connecting rod directly attached to the locking plate implant and the oblique rod, the locking plate implant and the oblique rod having a locked engagement therebetween from the direct attachment of said second connecting rod to the locking plate implant and the oblique rod.

2. The device of claim 1, further comprising a third connecting rod arranged to connect the oblique rod to one of the bones in the foot.

3. The device of claim 1, further comprising a locking screw inserted through an aperture of the vertical rod that abuts the oblique rod.

4. The device of claim 1, the vertical rod including apertures for alignment of the vertical rod against an alignment jig, the alignment jig including apertures configured for alignment of the vertical rod, the oblique rod, the connecting rods and the locking plate implant.

5. The device of claim 1, wherein the oblique rod is circular in cross-section.

6. The device of claim 1, wherein the oblique rod is polygonal in cross-section.

7. The device of claim 1, wherein said locking plate implant is adapted for subcutaneous fitment against the ankle bone.

8. The device of claim 1, wherein said locking plate implant is permanently locked to the vertical rod and the oblique rod to permanently immobilize an ankle joint.

9. A locking rod fusion device, comprising:
   a vertical rod;
   an oblique rod having a posterior end and an anterior tip, the posterior end attached to the vertical rod, the oblique rod slanting downward slightly from the posterior end to the anterior tip to establish a slightly obtuse angle between the vertical rod and the oblique rod such that when the vertical rod is inserted through a plantar foot, the oblique rod is aligned for insertion through the medial column;
   a calcaneocuboid rod having a posterior end and an anterior tip, the posterior end attached to the vertical rod, the calcaneocuboid rod slanting downward slightly from the posterior end to the anterior tip to establish a slightly obtuse angle between the vertical rod and the calcaneocuboid rod such that when the vertical rod is inserted through a plantar foot, the calcaneocuboid rod is aligned for insertion through the calcaneocuboid joint;
   a first connecting rod directly attached to the calcaneocuboid rod and the oblique rod, the calcaneocuboid rod and the oblique rod having a locked engagement therebetween from the direct attachment of said first connecting rod to the calcaneocuboid rod and the oblique rod; and
   a second connecting rod directly attached to the calcaneocuboid rod and adapted to lock the calcaneocuboid rod to an adjacent bone of the plantar foot.

10. The device of claim 9, further comprising a locking screw inserted through an aperture of the vertical rod that abuts the calcaneocuboid rod.

11. A locking rod fusion device, comprising:
    a vertical rod;
    a locking plate lockingly attached to the vertical rod, the locking plate shaped to fit subcutaneously against an ankle bone, the locking plate including a plurality of apertures aligned with the vertical rod and with bones in the foot when fit against the ankle bone;
    a first connecting rod directly attached to the locking plate and to the vertical rod, the locking plate and the vertical rod having a locked engagement therebetween from the direct attachment of said first connecting rod to the locking plate and the vertical rod; and
    an oblique rod lockingly attached to the locking plate, the oblique rod having a posterior end and an anterior tip, the posterior end attached to the vertical rod, the oblique rod having an aperture aligned with one of the apertures of the locking plate, the oblique rod slanting downward slightly from the posterior end to the anterior tip to establish a slightly obtuse angle between the vertical rod and the oblique rod such that when the vertical rod is inserted through a plantar foot, the oblique rod is aligned for insertion through the medial column.

12. The device of claim 11, the locking plate being an implant adapted for subcutaneous fitment against the ankle bone.

13. The device of claim 11, wherein said locking plate implant is permanently locked to the vertical rod and the oblique rod to permanently immobilize an ankle joint.

14. The device of claim 11, the locking plate being an implant adapted for subcutaneous fitment against the ankle bone.

15. The device of claim 11, further comprising a second connecting rod directly attached to the locking plate and the oblique rod, the locking plate and the oblique rod having a locked engagement therebetween from the direct attachment of said second connecting rod to the locking plate and the oblique rod via the aligned apertures thereof.

16. The device of claim 15, wherein said locking plate implant is permanently locked to the vertical rod and the oblique rod to permanently immobilize an ankle joint.

17. The device of claim 15, the locking plate being an implant adapted for subcutaneous fitment against the ankle bone.

18. The device of claim 17, wherein said locking plate implant is permanently locked to the vertical rod and the oblique rod to permanently immobilize an ankle joint.

19. The device of claim 18, the vertical rod including apertures for alignment of the vertical rod against an alignment jig, the alignment jig including apertures configured for alignment of the vertical rod, the oblique rod, the connecting rods and the locking plate.

\* \* \* \* \*